US00PP35495P2

(12) United States Plant Patent
Michael

(10) Patent No.: US PP35,495 P2
(45) Date of Patent: Nov. 21, 2023

(54) ***XSEMPONIUM* PLANT NAMED 'DESTINY'**

(50) Latin Name: **x *Semponium***
Varietal Denomination: Destiny

(71) Applicant: Surreal Succulents, Marazion (GB)

(72) Inventor: Daniel Michael, Marazion (GB)

(73) Assignee: SURREAL SUCCULENTS, Marazion (GB)

( * ) Notice: Subject to any disclaimer, the term of this patent is extended or adjusted under 35 U.S.C. 154(b) by 0 days.

(21) Appl. No.: 18/110,002

(22) Filed: Feb. 15, 2023

(30) Foreign Application Priority Data

Jul. 11, 2022 (QZ) ..... PBR 2022/1701

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of x *Semponium* plant named 'Destiny' that is characterized by its compact, dense growth habit with short stems, its foliage that is glossy, thick and sturdy, its large, strong rosettes that produce offsets after a year or two, and unique foliage coloration with intense dark purple all year round with raised veins when mature, in winter, dark purple with bright green centers.

2 Drawing Sheets

Botanical classification: x *Semponium.*
Variety denomination: 'Destiny'.

CROSS REFERENCE TO A RELATED APPLICATION

This application is related to a European plant breeders' rights application filed on Jul. 11, 2022, application No. 2022/1701. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of x *Semponium*, an interspecific hybrid plant and referred to hereinafter by its cultivar name, 'Destiny'. The new cultivar of x *Semponium* is a frost hardy succulent subshrub perennial grown for ornamental foliage use in landscapes and containers.

The new cultivar arose from an ongoing breeding program by the Inventor in Penzance, Cornwall, United Kingdom. The goal of the breeding program was to produce a new cultivar of x *Semponium* with unique foliage coloration, a compact growth habit, a dense and neat plant habit with production of many side shoots.

The new cultivar arose from a cross made by the Inventor in 2016 between *Sempervivum ciliosum* 'Green Ice' (not patented) as the female parent and *Aeonium* 'Ice Warrior' (not patented) as the male parent. The Inventor selected 'Destiny' as a single unique plant amongst the seedlings that resulted from the above cross in 2018.

Asexual propagation of the new cultivar was first accomplished by the Inventor by stem cuttings in 2018 in Penzance, Cornwall, United Kingdom. Asexual propagation by stem cuttings, offshoots, root cuttings, and tissue culture using meristematic tissue has determined the characteristics to be stable and reproduced true to type in successive generations.

SUMMARY OF THE INVENTION

The following traits have been repeatedly observed and are determined to be the characteristics of the new cultivar. These attributes in combination distinguish 'Destiny' as a unique cultivar of x *Semponium.*

1. 'Destiny' exhibits a compact, dense growth habit with short stems.
2. 'Destiny' exhibits foliage that is glossy, thick and sturdy.
3. 'Destiny' exhibits large, strong rosettes that produce offsets after a year or two.
4. 'Destiny' exhibits unique foliage coloration with intense dark purple all year round with raised veins when mature, in winter; dark purple with bright green centers.

The female parent plant, 'Green Ice', differs from 'Destiny' in having foliage that is green in color, a flatter plant shape, a less robust growth habit, plant height and rosettes that are smaller in size, and foliage that does not have veiny markings. The male parent, 'Ice Warrior', differs from 'Destiny' in having longer stems, foliage that lacks raised veins and is green in color with purple-red margins and changes to solid green in winter. 'Destiny' can be most closely compared to the x *Semponium* cultivar 'Sienna' (U.S. Plant Pat. No. 34,201). 'Sienna' is similar to 'Destiny' in having a low growing habit. 'Sienna' differs from 'Destiny' in having foliage that is dark purple with green centers that lacks raised veins, leaves that are thinner, and a wider plant size, and in producing more offsets.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Surreal Succulents, Country Living, RHS, Perishable News, The English Garden, House Beautiful, Gardening Express, The Drurys, Plantipp, YouTube, Mr Fother Gills Blog, Press Reader, Gardening Etc, Twitter, Thompson Morgan, Nova, Alamy, Sandras Gardening Blog, Bourne Mouthecho, Richard Jacksons Garden, Exotic Plants Online, Tumblr, Pinterest, CA Sports Yahoo, Hortweek, Good House Keeping, Instagram, News Chain Online, Mandy Can U Dig It, Stadtundgruen, Prolandscapermagazine, Dergartenbau, Horticulture Connected, Gardeners Company, Boom in Business, Garden Drum, Wikipedia, Starts at 60, Mariannemajerus, Heralds Scotland, CoWellsGC, Plews Garden Design, gbif, Irelandlive, Garden Form, Gardens without borders, muckrack, Falmouthpacket, Capital Gardens, Flipboard, Cornwall365, Gaertner-und-florist, Manojmaldegardendesign, Suttons, Bilibili, Talking Dirty Captivate FM, Jobearnshaw, Janeperrone, FT, Greenhousemag, Martinseewald, Nurserymag, Listennotes, Forum bcss, BCC, bartongrange, gabot, gardeners-club, Visions Pictures, Ellen Mary Gardening, Grey Journal, Promessedefleurs, Charlested, and The Critic.

BRIEF DESCRIPTION OF THE DRAWINGS

The accompanying color photographs illustrate the overall appearance and distinct characteristics of a one-year-old plant of 'Destiny' as grown outdoors in a 3-liter container in Waddinxveen, The Netherlands.

The photograph in FIG. 1 provides a side view of a plant of 'Destiny' in summer.

Figure 1:
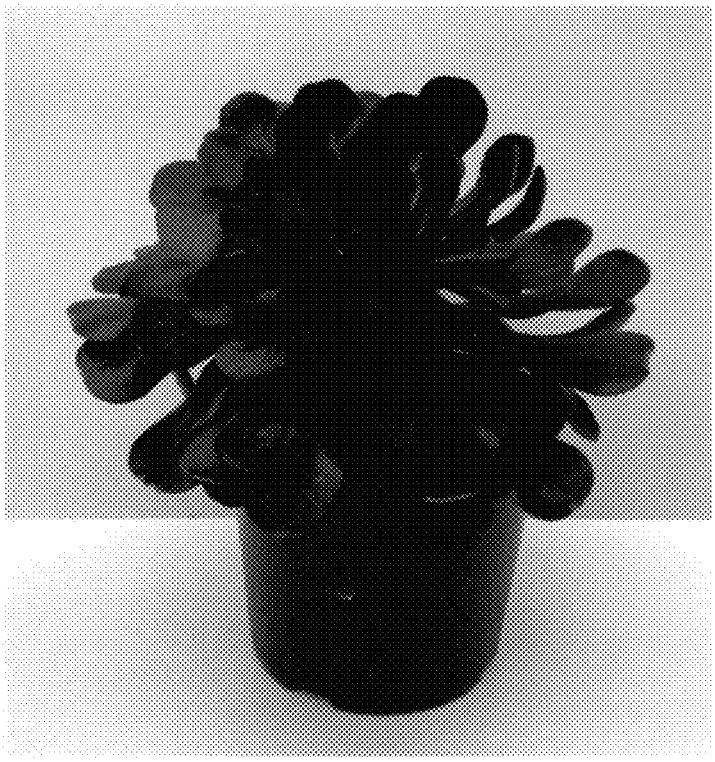
Figure 2:
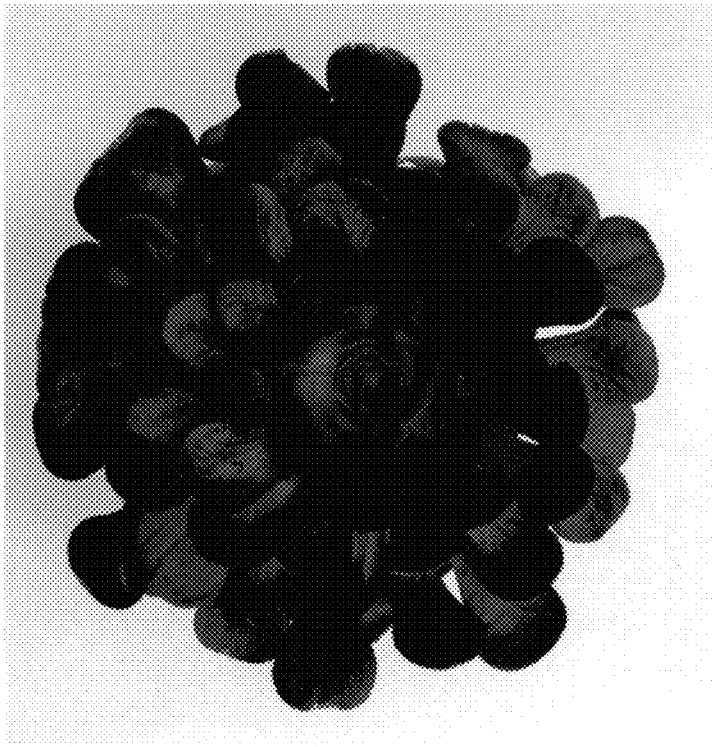

The photograph in FIG. 2 provides a top view of a plant of 'Destiny' in summer.

Figure 3:
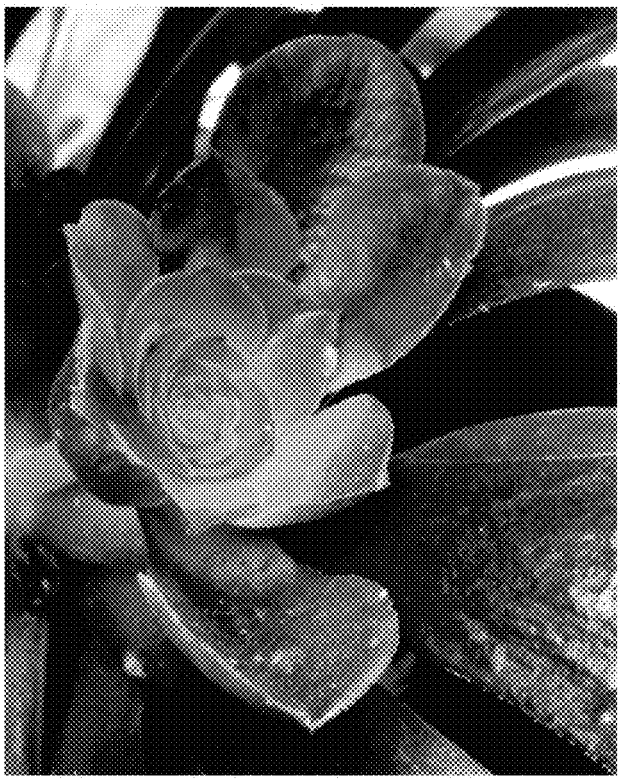

The photograph in FIG. 3 provides a close-up view of a an offshoot rosette 'Destiny'.

Figure 4:
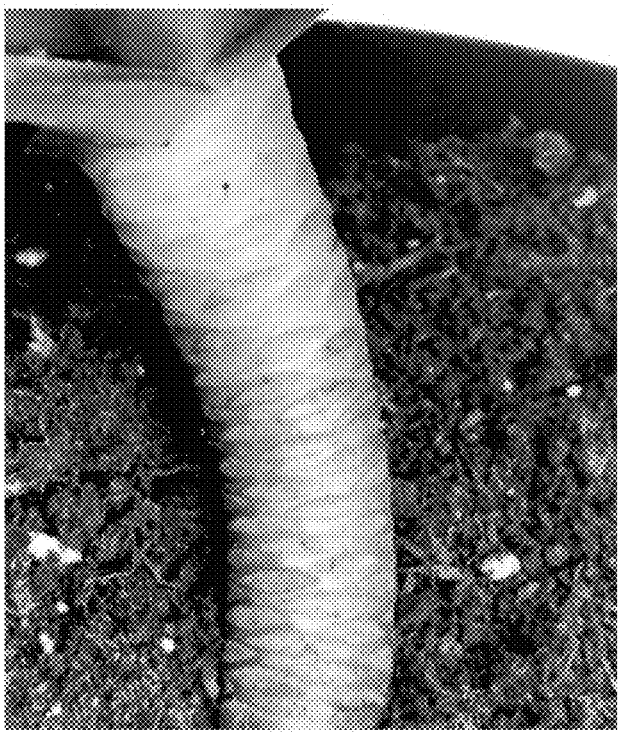

The photograph in FIG. 4 provides a close-up view of the stem of 'Destiny'.

The colors in the photographs may differ slightly from the color values cited in the detailed botanical description, which accurately describe the colors of the new x *Semponium.*

DETAILED BOTANICAL DESCRIPTION

The following is a detailed description of the new cultivar as observed on 1-year-old plants of 'Destiny' as grown outdoors in 3-liter containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Evergreen succulent perennial.

*Plant shape.*—Conical, compact, dense.

*Plant habit.*—Compact, 1 large rosette on a short stem, produces offsets.

*Height and spread.*—Reaches up to 21 cm in height and 41 cm in width as a one-year-old plant in a container.

*Cold hardiness.*—At least hardy to −5° C., has not been tested in colder climates.

*Diseases and pests.*—No susceptibility or resistance to diseases or pests has been observed.

*Root description.*—Fibrous.

*Propagation.*—Stem cuttings, offshoots, root cuttings, and tissue culture.

*Root development.*—Roots initiate in an average of 6 weeks and fully root as a young plant in a P7 container in 2 months.

*Growth rate.*—Moderate.

Stem description:

*Stem shape.*—Cylindrical.

*Stem size.*—Average of 3 cm in width and up to 9 cm in length.

*Stem surface.*—Smooth with leaf scars at the base.

*Stem arrangement.*—1 main stem, 1 offset.

*Stem aspect.*—Average of 60° from horizontal.

*Internode length.*—Up to 6 cm.

*Stem color.*—N144C and 144D, scars 199A.

Foliage description:

*Leaf shape.*—Spathulate.

*Leaf division.*—Simple.

*Leaf arrangement.*—Rosette.

*Leaf quantity.*—Average of 130 to 140 per rosette.

*Leaf base.*—Narrowly cuneate.

*Leaf apex.*—Rounded.

*Leaf venation.*—Veins are similar to color as leaves on both surfaces, raised on upper surface on mature leaves.

*Leaf margins.*—Ciliate.

*Leaf attachment.*—Sessile.

*Leaf orientation.*—Flat to slightly concave.

*Leaf substance.*—Succulent.

*Leaf thickness.*—1.25 mm to 2.25 mm.

*Leaf surface.*—Both surfaces smooth, glossy with veiny markings.

*Leaf color.*—Young leaves upper surface; 143B to 143C, margins N186C, young leaves lower surface; 143C, margins N186C, mature leaves upper surface; 145C, speckled (veiny markings) with 183B in the base and center, tip 186C and N186A, mature leaves lower surface; base 145B, speckled (veiny markings) with 183B and 187A towards the top, winter both surfaces; N186A with 145C in centers and on veins.

*Leaf size.*—Average of 18 cm in length, 6.2 cm in width (toward apex), 1.8 cm in width (at base).

*Rosette size.*—An average of 41 cm in diameter (large rosette), 9.5 cm in diameter (offset).

Flower description: No flowers have been observed to date.

It is claimed:

1. A new and distinct variety of x *Semponium* plant named 'Destiny' as described and illustrated herein.

* * * * *